US012674037B2

(12) United States Patent
Kim et al.

(10) Patent No.: US 12,674,037 B2
(45) Date of Patent: Jul. 7, 2026

(54) METHOD FOR MANUFACTURING A RECYCLED MATERIAL COMPOSITION

(71) Applicant: SK CHEMICALS CO., LTD., Gyeonggi-do (KR)

(72) Inventors: Ji-Hun Kim, Gyeonggi-do (KR); Gayeong Ryu, Gyeonggi-do (KR); Kwang-Woo Park, Gyeonggi-do (KR); Joong Ki Lee, Gyeonggi-do (KR)

(73) Assignee: SK CHEMICALS CO., LTD., Gyeonggi-do (KR)

( * ) Notice: Subject to any disclaimer, the term of this patent is extended or adjusted under 35 U.S.C. 154(b) by 51 days.

(21) Appl. No.: 18/713,702

(22) PCT Filed: Mar. 12, 2024

(86) PCT No.: PCT/KR2024/003183
§ 371 (c)(1),
(2) Date: May 28, 2024

(87) PCT Pub. No.: WO2025/048092
PCT Pub. Date: Mar. 6, 2025

(65) Prior Publication Data
US 2025/0376571 A1     Dec. 11, 2025

(30) Foreign Application Priority Data
Aug. 31, 2023     (KR) ........................ 10-2023-0115512

(51) Int. Cl.
| | |
|---|---|
| *C08J 11/26* | (2006.01) |
| *B29B 17/00* | (2006.01) |
| *B29C 48/285* | (2019.01) |
| *B29C 48/78* | (2019.01) |
| *C07C 67/03* | (2006.01) |
| *C07C 67/52* | (2006.01) |
| *C07C 67/54* | (2006.01) |
| *C07C 67/56* | (2006.01) |
| *C07C 69/82* | (2006.01) |
| *B29C 48/00* | (2019.01) |
| *B29K 67/00* | (2006.01) |

(52) U.S. Cl.
CPC .............. *C08J 11/26* (2013.01); *B29B 17/00* (2013.01); *B29C 48/287* (2019.02); *B29C 48/78* (2019.02); *C07C 67/03* (2013.01); *C07C*

*67/52* (2013.01); *C07C 67/54* (2013.01); *C07C 67/56* (2013.01); *C07C 69/82* (2013.01); *B29B 2017/001* (2013.01); *B29C 48/0011* (2019.02); *B29K 2067/003* (2013.01); *C08J 2367/02* (2013.01)

(58) Field of Classification Search
CPC . C08J 11/04; C08J 11/26; B29B 17/00; B29B 17/001; C07C 29/82; C07C 69/82; B29C 48/011
See application file for complete search history.

(56) References Cited

U.S. PATENT DOCUMENTS

| | | | |
|---|---|---|---|
| 4,255,295 A * | 3/1981 | Regnault ................. | C08J 11/06 |
| | | | 528/502 A |
| 2023/0092877 A1 | 3/2023 | Turan et al. | |

FOREIGN PATENT DOCUMENTS

| | | | | |
|---|---|---|---|---|
| CN | 108396392 A * | 8/2018 | ............. | D01D 5/096 |
| EP | 4375267 A1 * | 5/2024 | ............. | C07C 69/82 |
| JP | 2002332379 A | 11/2002 | | |
| JP | 2003-055300 A | 2/2003 | | |
| KR | 20110078934 A | 7/2011 | | |
| KR | 20220119059 A | 8/2022 | | |
| KR | 102504202 B1 | 2/2023 | | |
| WO | WO-2021123299 A1 * | 6/2021 | ............. | C08J 11/105 |

OTHER PUBLICATIONS

International Search Report for the PCT Application No. PCT/KR2024/003183 by the International Searching Authority on Jun. 21, 2024.
Extended European Search Report for European Patent Application No. 24730179.9 issued by the European Patent Office on Jan. 30, 2026.

* cited by examiner

*Primary Examiner* — Yate' K Cutliff
(74) *Attorney, Agent, or Firm* — IP & T GROUP LLP

(57) ABSTRACT

The present invention relates to a process for preparing a recycled raw material composition using depolymerization of waste polyester. The preparation process comprises (1) pretreating a waste polyester with an apparent density of 0.1 kg/L or less to have an apparent density of 0.5 kg/L or more; (2) depolymerizing the pretreated waste polyester; and (3) purifying the reactant obtained through the depolymerization.

14 Claims, No Drawings

METHOD FOR MANUFACTURING A RECYCLED MATERIAL COMPOSITION

This application is a national stage application of PCT/KR2024/003183 filed on Mar. 12, 2024, which claims priority of Korean patent application number 10-2023-0115512 filed on Aug. 31, 2023. The disclosure of each of the foregoing applications is incorporated herein by reference in its entirety.

TECHNICAL FIELD

The present invention relates to a process for preparing a recycled raw material composition capable of preparing a recycled raw material composition with high purity in high yield through a recycling process (pretreatment and depolymerization) of waste polyester, and a recycled raw material composition prepared therefrom.

BACKGROUND ART

Polyester, among polymers, is widely used as a material for containers for beverages, various packaging films, interior and exterior materials such as panels, shelves, and partitions, and the like by virtue of its excellent mechanical strength, thermal resistance, transparency, and gas barrier properties.

As a result, waste of plastics such as polyester is generated at an unmanageable level every year. Recently, countries around the world have prepared regulations and plans for recycling waste plastic resources, including waste polyester.

Although physical or chemical recycling methods are used as methods of recycling waste polyester, physical recycling methods cannot guarantee purity and, therefore, are not widely adopted. Meanwhile, in chemical recycling methods, the ester bond of a waste polyester is severed to depolymerize the waste polyester. Reactions such as glycolysis, hydrolysis, methanolysis, and aminolysis are used. Glycolysis among them is to decompose a waste polyester by adding a glycol such as ethylene glycol or diethylene glycol. A recycled raw material such as bis(2-hydroxyethyl) terephthalate (BHET) is obtained.

However, the waste polyester varies in degree of contamination, shape, and apparent density depending on the environment in which it is collected. It may contain heterogeneous components rather than a single component; thus, the amount that can be depolymerized using a chemical recycling method is limited. Therefore, there are limits to increasing the yield of recycled raw materials to the required level.

DISCLOSURE OF INVENTION

Technical Problem

In order to solve the above conventional problems, an object of the present invention is to provide a process for preparing a recycled raw material composition capable of preparing a recycled raw material composition in high yield in an economical way even when a waste polyester, which has various degrees of contamination, shape, apparent density, and the like and has heterogeneous components, as well as a single component, is used as a raw material for depolymerization.

In addition, another object of the present invention is to provide a recycled raw material composition with high purity prepared from the above preparation process.

Solution to Problem

In order to solve the above problems, the present invention provides a process for preparing a recycled raw material composition that comprises (1) pretreating a waste polyester with an apparent density of 0.1 kg/L or less to have an apparent density of 0.5 kg/L or more; (2) depolymerizing the pretreated waste polyester; and (3) purifying the reactant obtained through the depolymerization.

In addition, the present invention provides a recycled raw material composition that is prepared by the above preparation process.

Advantageous Effects of Invention

In the present invention, a waste polyester is subjected to a pretreatment procedure to adjust the apparent density to a certain range or more, and the waste polyester whose apparent density has been adjusted is depolymerized to prepare a recycled raw material composition. Thus, it is possible to prepare a recycled raw material composition with high purity in high yield even when a waste polyester, which has various degrees of contamination, shape, apparent density, and the like and has heterogeneous components, as well as a single component, is used as a raw material for depolymerization.

Accordingly, the present invention can recycle waste polyester in an economical and efficient way.

BEST MODE FOR CARRYING OUT THE INVENTION

Hereinafter, the present invention will be described in detail. The present invention herein is not limited to the disclosures given below, but it may be modified into various forms as long as the gist of the invention is not changed.

In the present specification, the term "comprising" is intended to specify a particular characteristic, region, step, process, element, and/or component. It does not exclude the presence or addition of any other characteristic, region, step, process, element and/or component, unless specifically stated to the contrary.

Throughout the present specification, the terms first, second, and the like are used to describe various components. But the components should not be limited by the terms. The terms are used for the purpose of distinguishing one element from another.

All numbers and expressions related to the quantities of components, reaction conditions, and the like used herein are to be understood as being modified by the term "about" unless otherwise indicated.

In the present specification, a singular expression is interpreted to cover a plural number as well unless otherwise specified in the context.

As polyester is used in many fields, it is commercialized in various forms. Articles containing a polyester are composed of a polyester as a single component, or, if necessary, are composed of heterogeneous components in which a polyester is mixed with other components. Accordingly, a waste polyester derived from used products has various shapes, sizes, and compositions.

In order to be recycled, such a waste polyester is usually subjected to procedures such as removal of foreign substances and crushing. In such an event, the difference in degree of crushing a waste polyester may be expressed as apparent density (kg/L). The larger the apparent density, the more advantageous for a chemical recycling process of a waste polyester.

Specifically, the present inventors have discovered that when a chemical recycling process is carried out using a waste polyester as a raw material for depolymerization, and when a waste polyester with a low apparent density is used, the amounts of a waste polyester and reactants (e.g., glycol-based compounds) that can be employed in the depolymerization process are limited; as a result, the capacity for producing a recycled raw material composition through the chemical recycling process of a waste polyester is reduced. In addition, a waste polyester, which has heterogeneous components (e.g., a polyester mixed with a polyolefin, a polyamide, a polytetrafluoroethylene, or the like), rather than a single component, and has a lower apparent density, makes difficult the separation of the heterogeneous components and the removal of impurities during the purification procedure after the depolymerization procedure. Thus, the purity and yield of a recycled raw material composition derived from a waste polyester are also significantly reduced.

As described above, the present inventors have discovered that the apparent density of a waste polyester, which is a raw material for depolymerization, is a factor that greatly affects the efficiency of a chemical recycling process and the purity and yield of a recycled raw material composition. Based on this, the present inventors have adopted a pretreatment procedure to control the apparent density of a waste polyester to enhance overall process efficiency and prepare a recycled raw material composition with high purity in high yield.

That is, in the present invention, the apparent density of a waste polyester is increased to a certain range or more through a specific pretreatment procedure, and a chemical recycling process comprising a depolymerization procedure is then carried out, which will be described in detail below.

Process for Preparing a Recycled Raw Material Composition

The process for preparing a recycled raw material composition according to the present invention comprises (1) pretreating a waste polyester with an apparent density of 0.1 kg/L or less to have an apparent density of 0.5 kg/L or more; (2) depolymerizing the pretreated waste polyester; and (3) purifying the reactant obtained through the depolymerization.

Step (1): Pretreatment to Control Apparent Density

According to the present invention, step (1) is a step of pretreating a waste polyester with an apparent density of 0.1 kg/L or less to have an apparent density of 0.5 kg/L or more.

When the apparent density of a waste polyester is 0.1 kg/L or less, the amount of a waste polyester and glycol-based compounds that can be employed in a depolymerization procedure are limited, which may reduce the depolymerization reaction efficiency. Accordingly, the apparent density of a waste polyester is adjusted to 0.5 kg/L or more through the pretreatment of step (1). When the apparent density of a waste polyester is adjusted to 0.5 kg/L or more, the surface area of the waste polyester increases, thereby significantly increasing the efficiency of a depolymerization reaction with a glycol-based compound, and insoluble components (foreign substances derived from heterogeneous components) in the reactant obtained through the depolymerization procedure may be present in the form of uniform small particles, making purification of the insoluble components easier.

Accordingly, in the present invention, the overall process efficiency is increased while the loss of recycled raw materials (e.g., bis(2-hydroxyethyl) terephthalate (BHET)) accompanying insoluble components is minimized, whereby it is possible to prepare a recycled raw material composition with high purity in high yield.

The apparent density of a waste polyester subjected to the pretreatment may specifically be 0.53 kg/L or more, 0.55 kg/L or more, 0.58 kg/L or more, 0.6 kg/L or more, 0.63 kg/L or more, 0.65 kg/L or more, 0.67 kg/L or more, 0.69 kg/L or more, 0.7 kg/L or more, 0.72 kg/L or more, 0.73 kg/L or more, 0.75 kg/L or more, 0.77 kg/L or more, or 0.8 kg/L or more (e.g., 0.52 to 0.8 kg/L, 0.56 to 0.79 kg/L, 0.61 to 0.78 kg/L, 0.64 to 0.78 kg/L, or 0.68 to 0.77 kg/L), in light of the purity and yield of the recycled raw material composition.

The pretreatment of a waste polyester is not particularly limited, but it may be carried out through melt extrusion using an extruder. As a waste polyester is pretreated through melt extrusion, the apparent density of the waste polyester can be readily adjusted to 0.5 kg/L or more, which is the desired level in the present invention. In such an event, in order to adjust the apparent density of a waste polyester to 0.5 kg/L or more, it is desirable to optimally control the melt extrusion conditions.

Specifically, according to the present invention, the melt extrusion may be carried out at a temperature of 250 to 300° C. and an extrusion speed of 100 to 350 rpm for 2 to 15 minutes. If the melt extrusion conditions are outside the above ranges, the waste polyester may be decomposed (deformed or lost) due to overheating, or standardization that can control the apparent density may become impossible.

The melt extrusion temperature refers to the barrel temperature of the extruder. Specifically, it may be 250 to 295° C., 250 to 290° C., 250 to 285° C., 250 to 280° C., 250 to 275° C., 255 to 275° C., or 260 to 270° C.

The melt extrusion speed refers to the screw rotation speed of the extruder. Specifically, it may be 110 to 330 rpm, 115 to 300 rpm, 120 to 280 rpm, 125 to 250 rpm, 130 to 230 rpm, 135 to 220 rpm, 140 to 210 rpm, or 145 to 205 rpm.

The melt extrusion time refers to the time the waste polyester resides in the screw of the extruder. Specifically, it may be 2 to 13 minutes, 2 to 10 minutes, 2.5 to 8 minutes, 2.5 to 7 minutes, 3 to 6 minutes, 3 to 5 minutes, or 2 to 5 minutes.

The extruder used for the melt extrusion is not particularly limited as long as it is a commonly known extruder. Specifically, it may be a single-screw extruder or a twin-screw extruder.

According to the present invention, no separate additives (organic additives or inorganic additives) may be added to the melt extrusion. That is, in the present invention, the apparent density of a waste polyester is not adjusted chemically, but physically through melt extrusion.

According to the present invention, a waste polyester whose apparent density has been adjusted to 0.5 kg/L or more through the pretreatment may have various forms. Specifically, the shape of the pretreated waste polyester may be spherical, oval, cylindrical, or prismatic, and, preferably, cylindrical. In addition, the size (longest length) of the pretreated waste polyester is not particularly limited, but it may specifically be 5 mm or less, 4 mm or less, 3 mm or less, 2 mm or less, or 1 mm or less (e.g., 0.5 to 5 mm, 1.5 mm to 4.5 mm, 2 to 4 mm, 2.5 to 3.5 mm, or 2 to 3 mm). As a result, the efficiency of the depolymerization reaction of a waste polyester can be increased while the handling convenience of the waste polyester is secured.

Meanwhile, according to the present invention, the waste polyester to be pretreated is not particularly limited as long as it is a waste containing a polyester. Specifically, it may comprise a waste polyester fabric (fiber), a waste polyester film, a waste polyester flake, a waste polyester powder, or a combination thereof.

Step (2): Depolymerization

According to the present invention, step (2) is a step of depolymerizing the waste polyester whose apparent density has been adjusted to 0.5 kg/L or more through the pretreatment in step (1). The depolymerization step may comprise (2-1) subjecting the waste polyester whose apparent density has been adjusted to depolymerization through a first glycolysis reaction at a temperature of 180 to 200° C. to obtain a first reactant; and (2-2) subjecting the first reactant to depolymerization at a temperature of 150 to 170° C. through a second glycolysis reaction to obtain a second reactant.

Specifically, step (2-1) may comprise a procedure of carrying out a glycolysis reaction for primarily severing the polymer chain of the waste polyester with a first glycol-based compound to obtain a first reactant (a first product).

The first glycol-based compound used in the depolymerization of step (2-1) is not particularly limited, but it may specifically comprise at least one selected from the group consisting of ethylene glycol, propylene glycol, and diethylene glycol.

The feeding amount of the first glycol-based compound is not particularly limited. Specifically, it may be 1 time or more, 2 times or more, or 3 times or more, and 7 times or less, 5 times or less, or 4 times or less (e.g., 1 to 7 times, 2 to 5 times, or 3 to 4 times) the weight of the pretreated waste polyester.

The depolymerization temperature in step (2-1) may be 180 to 200° C., specifically, 180 to 195° C., 180 to 193° C., 180 to 190° C., 180 to 188° C., or 180 to 185° C. In addition, the depolymerization time in step (2-1) is not particularly limited, but it may be 1 to 4 hours, 1 to 3 hours, or 1 to 2 hours from the time the temperature required for the first depolymerization is reached. As the depolymerization in step (2-1) is carried out within the above ranges in terms of temperature and time, the first glycolysis reaction of the waste polyester can be carried out smoothly, while minimizing the formation of side reactants such as diethylene glycol ester compounds.

The depolymerization in step (2-1) may be carried out in the presence of a catalyst that activates the first glycolysis reaction. The catalyst is not particularly limited as long as it is a commonly known catalyst, but it may specifically comprise a metal acetate, an anhydride thereof, or a hydrate thereof. More specifically, the catalyst may be at least one selected from the group consisting of zinc acetate, sodium acetate, cobalt acetate, and manganese acetate, a hydrate thereof, or anhydride thereof.

The feeding amount (the amount used) of the catalyst in step (2-1) is not particularly limited, but it may specifically be 0.01 to 5 parts by weight, 0.05 to 3 parts by weight, 0.1 to 2 parts by weight, 0.15 to 1 part by weight, 0.2 to 0.6 part by weight, or 0.2 to 0.4 part by weight, relative to 100 parts by weight of the waste polyester.

For example, the first glycolysis reaction in step (2-1) may be a reaction of a waste polyester and ethylene glycol in the presence of zinc acetate hydrate.

Step (2-2) may comprise a procedure of carrying out a glycolysis reaction for secondarily severing the first reactant obtained in step (2-1) with a second glycol-based compound to obtain a second reactant (a second product). The second reactant may refer to a reactant obtained through step (2).

The second glycol-based compound used in the depolymerization of step (2-2) is not particularly limited, but it may specifically comprise at least one selected from the group consisting of ethylene glycol, propylene glycol, and diethylene glycol. The second glycol-based compound may be derived from the depolymerization procedure of step (2-1) or may be further fed during the depolymerization procedure of step (2-2).

The feeding amount (the additional amount used in the second depolymerization) of the second glycol-based compound is not particularly limited, it may specifically be 1 time or more, 2 times or more, or 3 times or more, and 7 times or less, 5 times or less, or 4 times or less (e.g., 1 to 7 times, 2 to 5 times, or 3 to 4 times) the weight of the pretreated waste polyester.

The depolymerization temperature in step (2-2) may be 150 to 170° C. Specifically, it may be 150 to 165° C., 150 to 163° C., 150 to 160° C., 150 to 158° C., or 150 to 155° C. In addition, the depolymerization time in step (2-2) is not particularly limited, but it may be 1 to 4 hours, 1 to 3 hours, or 1 to 2 hours from the time the temperature required for the second depolymerization is reached. As the depolymerization in step (2-2) is carried out within the above ranges in terms of temperature and time, the second glycolysis reaction of the first reactant can be carried out smoothly, while minimizing the formation of impurities such as diethylene glycol ester compounds.

The depolymerization in step (2-2) may be carried out in the presence of a catalyst that activates the second glycolysis reaction. The catalyst may be derived from the depolymerization procedure of step (2-1) or may be further fed during the depolymerization procedure of step (2-2). The description of the catalyst is the same as the description of the catalyst in step (2-1) above; thus, a detailed description is omitted.

As depolymerization is carried out through steps (2-1) and (2-2), a reactant comprising crude bis(2-hydroxyethyl) terephthalate (crude-BHET) can be obtained in high yield.

Step (3): Purification

According to the present invention, step (3) is a step of purifying the reactant (depolymerization reactant) obtained through the depolymerization in step (2). The purification of the reactant may be carried out through various steps.

For example, according to the present invention, the purification in step (3) may comprise cooling the reactant to a temperature of 100 to 150° C. and pressurized-filtering the reactant at a pressure of 0.01 to 0.5 MPa. Specifically, in the pressurized filtration, the reactant is cooled through a reduced pressure flash and then subjected to solid-liquid separation through a pressurized filtration procedure using a filter aid. As a result, the reactant can be converted to a liquid reactant. As the pressurized filtration is carried out, solid foreign matters such as particulates and insoluble organic substances contained in the reactant are removed, thereby increasing the purity and yield of the recycled raw material composition.

The temperature at which the reactant is cooled through the reduced pressure flash may specifically be 100 to 135° C., 105 to 125° C., or 110 to 120° C. In addition, the pressure for carrying out the reduced pressure flash is not particularly limited, but it may specifically be 200 Torr or less, 150 Torr or less, 100 Torr or less, 50 Torr or less, or 30 Torr or less, and 5 Torr or more, 8 Torr or more, 10 Torr or more, or 15 Torr or more (e.g., 5 to 200 Torr, 10 to 100 Torr, or 15 to 50 Torr).

The reactant cooled through the reduced pressure flash may have a pressurized filtration rate of 1.5 L/minute or more. Specifically, the pressurized filtration rate of the reactant may be 2 L/minute or more, 2.5 L/minute or more, 3 L/minute or more, 3.5 L/minute or more, 4 L/minute or more, 4.5 L/minute or more, 5 L/minute or more, or 5.5 L/minute or more (e.g., 1.5 to 6 L/minute, 3 to 5.7 L/minute, 4 to 5.6 L/minute, or 4.5 to 5.5 L/minute). Since the pressurized filtration rate of the reactant is high in the present invention as described above, the overall process efficiency can be high. This improvement in pressurized filtration rate is possible by adjusting the apparent density of a waste polyester to 0.5 kg/L or more to secure good separation between heterogeneous components in the waste polyester.

Meanwhile, the filter aid is not particularly limited as long as it is commonly known, but it may specifically comprise at least one selected from the group consisting of diatomaceous earth, perlite, and asbestos powder.

According to the present invention, the purification in step (3) may comprise treating the reactant with an ion-exchange resin. Specifically, the treatment may be carried out by passing the reactant through an ion-exchange resin or adding an ion-exchange resin to the reactant. As the above procedure is carried out, ionic impurities contained in the reactant may be removed to obtain a reactant with high purity.

The ion-exchange resin may be a cation-exchange resin, an anion-exchange resin, an amphoteric ion-exchange resin, a chelate resin, or a combination thereof, commonly known.

The cation-exchange resin may specifically comprise a strongly acidic cation-exchange resin having a sulfonic acid group ($-SO_3H$) or a weakly acidic cation-exchange resin having a carboxyl group ($-COOH$). The anion-exchange resin may comprise a strongly basic anion-exchange resin in the form of a quaternary ammonium salt or a weakly basic anion-exchange resin having a primary to tertiary amino group. The chelate resin may be a polymer resin having a reactive functional group such as acetate or phosphate that chelates metal ions such as sodium, copper, nickel, zinc, and manganese.

When the treatment is carried out by adding the ion-exchange resin to the reactant, the feeding amount (the amount used) of the ion-exchange resin is not particularly limited, but it may be 1 time or more, 2 times or more, 3 times or more, or 5 times or more, and 20 times or less, 15 times or less, 10 times or less, or 8 times or less (e.g., 1 to 20 times, 2 to 15 times, 3 to 10 times, or 5 to 8 times) the weight of the catalyst used in the depolymerization of step (2). In addition, the feeding amount (the amount used) of the ion-exchange resin may be 1 part by weight or more, 2 parts by weight or more, 3 parts by weight or more, or 5 parts by weight or more, and 50 parts by weight or less, 20 parts by weight or less, 15 parts by weight or less, 10 parts by weight or less, or 7 parts by weight or less (e.g., 1 to 50 parts by weight, 3 to 20 parts by weight, or 5 to 10 parts by weight), relative to 100 parts by weight of the waste polyester of step (2).

When the treatment is carried out by passing the reactant to the ion-exchange resin, the ion-exchange resin may be in the form of particles having a predetermined size. Specifically, the treatment for removing ionic impurities may be carried out by passing the reactant (e.g., the liquid reactant) through a column filled with ion-exchange resin particles having a particle size of 0.3 to 1.5 mm, 0.5 to 1.3 mm, or 0.7 to 1.0 mm.

According to the present invention, the purification in step (3) may comprise cooling and crystallizing the reactant. Specifically, the cooling crystallization may be carried out by lowering the temperature of the reactant. The temperature for cooling the reactant for crystallization of the reactant is not particularly limited, but it may specifically be 70° C. or lower, 60° C. or lower, 50° C. or lower, 40° C. or lower, 30° C. or lower, or 25° C. or lower, and may be 0° C. or higher, 5° C. or higher, 10° C. or higher, 15° C. or higher, or 20° C. or higher. As the cooling crystallization is carried out, acetate-based ester compounds and diethylene glycol ester compounds as impurities can be efficiently removed.

According to the present invention, the purification in step (3) may comprise distilling the reactant. Specifically, the distillation may be carried out by subjecting the reactant to vacuum distillation to obtain a product and subjecting the product thus obtained to thin film evaporation.

A glass distillation apparatus or a rotary evaporator may be used for the vacuum distillation of the reactant.

The vacuum distillation conditions are not particularly limited, but it may specifically be carried out at 150° C. or lower under a pressure of 0.1 to 200 Torr. More specifically, the pressure for carrying out the vacuum distillation may be 0.1 to 150 Torr, 0.2 to 100 Torr, 0.3 to 50 Torr, or 0.5 to 30 Torr. In addition, the temperature for carrying out the vacuum distillation may be 90° C. or higher, 100° C. or higher, or 110° C. or higher, and 145° C. or lower, 140° C. or lower, or 135° C. or lower (e.g., 90 to 150° C., 100 to 145° C., 120 to 135° C., or 100 to 130° C.).

Unreacted glycol-based compounds (e.g., ethylene glycol and diethylene glycol) contained in the reactant can be removed and recovered through the vacuum distillation, and the recovered glycol-based compounds can be reused in the depolymerization procedure of step (2).

A thin film evaporator comprising an evaporator, a wiper rotor, and a condenser may be used for the thin film evaporation of the reactant.

The thin film evaporation conditions are not particularly limited, but it may specifically be carried out at 150 to 250° C. under a pressure of 0.005 to 5 Torr. More specifically, the pressure for carrying out the thin film evaporation may be 0.005 to 4.5 Torr, 0.01 to 4 Torr, 0.05 to 3 Torr, or 0.07 to 1.5 Torr. In addition, the temperature for carrying out the thin film evaporation (internal thin film temperature of the thin film evaporator) may be 180 to 240° C., 185 to 230° C., 190 to 225° C., 195 to 220° C., or 200 to 220° C.

Oligomers (e.g., BHET dimer and BHET trimer) such as dimers or higher contained in the reactant can be efficiently removed through the thin film evaporation.

Meanwhile, the pressurized filtration, the ion exchange resin treatment, the cooling crystallization, the vacuum distillation, and the thin film evaporation for the purification of the reactant may be carried out depending on the type of impurities, and the order in which each step is carried out may also be selected appropriately.

In the present invention, a recycled raw material composition with high purity can be prepared in high yield through the purification in step (3). In particular, in the present invention, it is possible to prepare a recycled raw material composition in which the content of specific impurities is controlled to a certain range or less, and the content of bis(2-hydroxyethyl) terephthalate (BHET) as the desired component is significantly high.

Specifically, the composition of the recycled raw material composition obtained by the depolymerization of a waste polyester may be confirmed by measuring the peak area fraction (%) of the analyzed component out of the total peak area in a spectrum obtained by analyzing the recycled raw material composition by high-performance liquid chromatography (HPLC). In such an event, when the peak area fraction of components regarded as impurities is small, and when the peak area fraction of BHET as the desired component is high, the purity of the recycled raw material composition may be high.

For example, according to the present invention, when the recycled raw material composition obtained through steps (1) to (3) is analyzed by high-performance liquid chromatography (HPLC), the total sum (x+y) of the peak area fraction (x) of diethylene glycol ester (DEG-ester) compounds and the peak area fraction (y) of monohydroxyethyl terephthalate (MHET) may be less than 4.0%. Specifically, the total sum (x+y) of the peak area fractions may be 3.8% or less, 3.5% or less, 3.3% or less, 3.0% or less, 2.8% or less, 2.5% or less, 2.3% or less, 2.0% or less, 1.9% or less, 1.5% or less, 1.3% or less, 1.0% or less, or 0.8% or less (e.g., 0 to 3.5%, 0.3 to 3.0%, 0.5 to 2.5%, or 0.8 to 2.0%). If the diethylene glycol ester (DEG-ester) compounds remain in the recycled raw material composition, the melting point of a recycled polyester resin prepared using the recycled raw material composition is lowered, thereby deteriorating the thermal resistance of the recycled polyester resin. However, since the content of the diethylene glycol ester (DEG-ester) compounds in the recycled raw material composition of the present invention is controlled to a minimum, it can be advantageously used as a polymerization raw material for preparing a recycled polyester resin with excellent thermal resistance.

The diethylene glycol ester (DEG-ester) compounds may specifically comprise 2-hydroxyethyl[2-(2-hydroxyethoxy)ethyl] terephthalate (DEG-ester-1), bis[2-(2-hydroxyethoxy)ethyl]benzene-1,4-dicarboxylate (DEG-ester-2), or a combination thereof.

According to the present invention, when the recycled raw material composition obtained through steps (1) to (3) is analyzed by high-performance liquid chromatography (HPLC), the peak area fraction of an acetate-based ester (HA-ester) compound may be less than 0.4%. Specifically, the peak area fraction of an acetate-based ester (HA-ester) compound may be 0.35% or less, 0.3% or less, 0.25% or less, 0.23% or less, 0.2% or less, 0.18% or less, 0.15% or less, 0.13% or less, 0.1% or less, 0.09% or less, 0.07% or less, 0.05% or less, or 0.03% or less (e.g., 0 to 0.35%, greater than 0 to 0.3%, 0.01 to 0.25%, 0.03 to 0.2%, or 0.05 to 0.15%). If the acetate-based ester (HA-ester) compound remains in the recycled raw material composition, it may act as a terminator chain that inhibits the growth of a polymer chain when a recycled polyester resin is prepared using the recycled raw material composition, thereby deteriorating the thermal resistance of the recycled polyester resin. However, since the content of the acetate-based ester (HA-ester) compound in the recycled raw material composition of the present invention is controlled to a minimum, it can be advantageously used as a polymerization raw material for preparing a recycled polyester resin with excellent thermal resistance.

The acetate-based ester (HA-ester) compound may comprise 2-hydroxyethyl(2-acetoxyethyl) terephthalate.

According to the present invention, when the recycled raw material composition obtained through steps (1) to (3) is analyzed by high-performance liquid chromatography (HPLC), the peak area fraction of bis(2-hydroxyethyl) terephthalate (BHET) may be 95% or more. Specifically, the peak area fraction of bis(2-hydroxyethyl) terephthalate (BHET) may be 95.5% or more, 96% or more, 96.5% or more, 97% or more, 97.5% or more, 98% or more, 98.5% or more, 99% or more, 99.5% or more, or 100% (e.g., 95 to 100%, 96 to 99%, 96 to 98%, or 96.5 to 98%). As described above, since the recycled raw material composition of the present invention has a significantly high peak area fraction of bis(2-hydroxyethyl) terephthalate (BHET) as the desired component, it is possible to achieve high yield with high purity.

According to the present invention, when a recycled raw material composition is prepared through steps (1) to (3), the process yield (Y) according to the following Equation 1 may be 80% or more. Specifically, the process yield (Y) may be 81% or more, 81.5% or more, 82% or more, 82.5% or more, 83% or more, 83.5% or more, 84% or more, 84.5% or more, 85% or more, 85.5% or more, 86% or more, 86.5% or more, 87% or more, 88% or more, or 90% or more (e.g., 80 to 99%, 81 to 95%, 82 to 90%, or 84 to 88%).

$$Y\ (\%) = (W_1/W_2) \times 100 \qquad \text{[Equation 1]}$$

In Equation 1, $W_1$ is the weight of the recycled raw material composition obtained through steps (1) to (3) (actual weight of the recycled raw material composition obtained through the chemical recycling process), and $W_2$ is the theoretical weight of the recycled raw material composition prepared from the waste polyester used in step (1) (theoretical weight of the recycled raw material composition that can be obtained through a chemical recycling process of a waste polyester).

Recycled Raw Material Composition

The recycled raw material composition according to the present invention is prepared by the process for preparing a recycled raw material composition described above. Specifically, the recycled raw material composition may comprise recycled bis(2-hydroxyethyl) terephthalate (r-BHET) formed by the depolymerization of a waste polyester in a high content.

According to the present invention, since the recycled raw material composition comprises recycled bis(2-hydroxyethyl) terephthalate (r-BHET) in a high content while the content of impurities (e.g., MHET, DEG-ester, HA-ester, BHET dimer, BHET trimer, and the like) is controlled to a certain range or less, it can be advantageously used in the preparation of a recycled polyester resin. In particular, since the recycled bis(2-hydroxyethyl) terephthalate (r-BHET) contained in the recycled raw material composition has crystallinity and high purity, it can have physical properties equivalent to those of virgin bis(2-hydroxyethyl) terephthalate (virgin BHET). Accordingly, when a recycled polyester resin is prepared using the recycled bis(2-hydroxyethyl) terephthalate (r-BHET), it is possible to provide a recycled polyester resin with excellent thermal resistance, weatherability, color characteristics, and the like.

MODE FOR THE INVENTION

Hereinafter, the present invention will be described in more detail with reference to embodiments. However, these examples are provided only for illustration purposes, and the present invention is not limited thereto.

Example 1

Step (1): Pretreatment

A waste polyester fabric with an apparent density of 0.1 kg/L or less was fed to a twin-screw extruder and subjected to a pretreatment procedure by melt extrusion at a barrel temperature of 250° C. and an extrusion speed of 200 rpm for 3 minutes to obtain 1,000 g of a waste polyester fabric with an adjusted apparent density.

Step (2): Depolymerization

A first reactor made of stainless steel (SUS) was charged with 1,000 g of the waste polyester fabric obtained above, 2,000 g of ethylene glycol, and 15.0 g of zinc acetate anhydride. The temperature inside the first reactor was raised to 180° C., and a first depolymerization (first glycolysis reaction) was carried out for 2 hours to obtain a first reactant. Subsequently, the first reactant thus obtained was transferred to a second reactor and cooled to 150° C. Then, 2,000 g of ethylene glycol was further fed to the second reactor, and a second depolymerization (second glycolysis reaction) was carried out for 2 hours while the reactor temperature was maintained at 150° C. to obtain a second reactant.

Step (3): Purification

The second reactant obtained above was cooled to 120° C. through a reduced pressure flash and then subjected to high-temperature, pressurized filtration (solid-liquid separation) to obtain a liquid reactant.

The liquid reactant obtained was passed through a column filled with an ion-exchange resin (BC107(H) of Bonlite) to remove ionic impurities to obtain a mixture comprising recycled bis(2-hydroxyethyl) terephthalate (r-BHET) and ethylene glycol.

The mixture was transferred to a 10-liter distillation apparatus, and vacuum distillation was carried out at 130° C. to remove (recover) unreacted ethylene glycol. Subsequently, the third reactant from which ethylene glycol had been removed was subjected to thin film evaporation at 220° C. and 0.08 Torr in a thin film evaporator (VKL70-4S of VTA) to obtain a fourth reactant from which oligomers of dimers or higher had been removed.

Thereafter, for adsorption-crystallization, the fourth reactant and distilled water were charged to a 20-liter glass reactor and dissolved at a temperature of 70° C. Then, activated carbon was added thereto, followed by stirring for 30 minutes and filtration thereof. Next, the filtrate obtained by the filtration was cooled to room temperature to crystallize the same, filtered again, and dried in a vacuum oven, thereby preparing a recycled raw material composition comprising recycled bis(2-hydroxyethyl) terephthalate.

Example 2

A recycled raw material composition was prepared through the same procedure as in Example 1, except that a waste polyester banner was used instead of the waste polyester fabric, and the pretreatment conditions were adjusted as shown in Table 1 below.

Example 3

A recycled raw material composition was prepared through the same procedure as in Example 1, except that a waste polyester film scrap was used instead of the waste polyester fabric, and the pretreatment conditions were adjusted as shown in Table 1 below.

Example 4

A recycled raw material composition was prepared through the same procedure as in Example 1, except that the pretreatment conditions of the waste polyester fabric were adjusted as shown in Table 1 below.

Example 5

A recycled raw material composition was prepared through the same procedure as in Example 1, except that the pretreatment conditions of the waste polyester fabric were adjusted as shown in Table 1 below.

Example 6

A recycled raw material composition was prepared through the same procedure as in Example 1, except that the pretreatment conditions of the waste polyester fabric were adjusted as shown in Table 1 below.

Comparative Example 1

A recycled raw material composition was prepared through the same procedure as in Example 1, except that the pretreatment of the waste polyester fabric was omitted.

Comparative Example 2

A recycled raw material composition was prepared through the same procedure as in Example 2, except that the pretreatment of the waste polyester banner was omitted.

Comparative Example 3

A recycled raw material composition was prepared through the same procedure as in Example 3, except that the pretreatment of the waste polyester film scrap was omitted.

Comparative Example 4

A recycled raw material composition was prepared through the same procedure as in Example 1, except that a waste polyester fabric with an apparent density of 0.1 kg/L or less was fed to a reactor capable of pulverization and crystallization and subjected to a pretreatment procedure (heat set) by heating at 220° C. for 60 minutes, instead of being subjected to pretreatment by melt extrusion, to obtain a waste polyester fabric with an adjusted apparent density.

Comparative Example 5

A recycled raw material composition was prepared through the same procedure as in Comparative Example 4, except that a waste polyester banner was used instead of the waste polyester fabric.

Comparative Example 6

A recycled raw material composition was prepared through the same procedure as in Comparative Example 4, except that a waste polyester film scrap was used instead of the waste polyester fabric.

Test Example

The materials obtained in Examples 1 to 6 and Comparative Examples 1 to 6 were each tested by the following methods. The results are shown in Tables 1 and 2 below.

(1) High-Performance Liquid Chromatography (HPLC)

0.01 g of a sample (recycled raw material composition) was diluted in 20 ml of methanol, which was analyzed by high-performance liquid chromatography (HPLC) (model: Waters e2695, column: C18 (4.6×250 mm), 5 μm, UV detector: 242 nm, injection volume: 10 μl, eluent (gradient) A: $H_2O+H_3PO_4$, B: acetonitrile). Thereafter, the peak area fractions (%) of the following components among the total peak area of HPLC were confirmed.

MHET: monohydroxyethyl terephthalate

BHET: bis(2-hydroxyethyl) terephthalate,

DEG-ester-1: 2-hydroxyethyl[2-(2-hydroxyethoxy)ethyl] terephthalate

DEG-ester-2: bis[2-(2-hydroxyethoxy)ethyl]benzene-1,4-dicarboxylate

HA-ester: 2-hydroxyethyl(2-acetoxyethyl) terephthalate

Dimer: BHET dimer

Trimer: BHET trimer (2) Apparent Density (kg/L)

Each waste polyester was filled without pressure in a 2-liter flask of known volume, the weight was measured, and the apparent density was calculated using the relationship between the measured weight and flask volume. The results are shown in Tables 1 and 2 below.

14

(3) Pressurized Filtration Rate (L/Minute)

The pressurized filtration rate of the depolymerization reactant (second reactant) was measured under the following conditions. The results are shown in Tables 1 and 2 below. Pressurized filter area: 700 cm$^2$; —pressurized filter mesh size: 1 μm; —pressurized pressure: 0.01 to 0.5 MPa (4) Process Yield (%)

The process yield of the recycled raw material composition was calculated according to the following Equation 1.

$$Y\ (\%) = (W_1/W_2) \times 100 \qquad \text{[Equation 1]}$$

In Equation 1, $W_1$ is the weight of the recycled raw material composition obtained through steps (1) to (3), and $W_2$ is the theoretical weight of the recycled raw material composition prepared from the waste polyester used in step (1).

TABLE 1

| | | | Ex. 1 | Ex. 2 | Ex. 3 | Ex. 4 | Ex. 5 | Ex. 6 |
|---|---|---|---|---|---|---|---|---|
| Waste polyester | | Type of raw material for depolymerization | Waste fabric | Waste banner | Waste film scrap | Waste fabric | Waste fabric | Waste fabric |
| | | Pretreatment method | Extrusion | Extrusion | Extrusion | Extrusion | Extrusion | Extrusion |
| | | Melt extrusion temp./ Heat set temp. (° C.) | 250 | 250 | 270 | 250 | 250 | 320 |
| | | Melt extrusion speed (rpm) | 200 | 150 | 150 | 50 | 400 | 200 |
| | | Melt extrusion time (min.) | 3 | 5 | 5 | 20 | 1 | 3 |
| | Apparent density (kg/L) | Before pretreatment | 0.05 | 0.03 | 0.09 | 0.05 | 0.05 | 0.05 |
| | | After pretreatment | 0.74 | 0.77 | 0.69 | Apparent density not measurable due to excessive decomposition or non-melting | | |
| Recycled raw material composition | HPLC (Area %) | MHET | 0.39 | 1.72 | 1.10 | — | | |
| | | BHET | 97.98 | 96.58 | 97.64 | | | |
| | | DEG-ester-1 | 0.36 | 0.61 | 0.62 | | | |
| | | DEG-ester-2 | 0.10 | 0.09 | 0.16 | | | |
| | | HA-ester | 0.05 | 0.08 | 0.12 | | | |
| | | Dimer | 0.23 | 0.90 | 0.22 | | | |
| | | Trimer | 0.02 | 0.00 | 0.02 | | | |
| | | Others | 0.9 | 0.0 | 0.1 | | | |
| | Pressurized filtration rate (L/min.) | | 5.40 | 5.50 | 4.70 | | | |
| | Process yield (%) | | 87.1 | 85.1 | 82.8 | | | |

45

TABLE 2

| | | | C. Ex. 1 | C. Ex. 2 | C. Ex. 3 | C. Ex. 4 | C. Ex. 5 | C. Ex. 6 |
|---|---|---|---|---|---|---|---|---|
| Waste polyester | | Type of raw material for depolymerization | Waste fabric | Waste banner | Waste film scrap | Waste fabric | Waste banner | Waste film scrap |
| | | Pretreatment method | Not performed | Not performed | Not performed | Heat set | Heat set | Heat set |
| | | Melt extrusion temp./ Heat set temp. (° C.) | — | — | — | 220 | 220 | 220 |
| | | Melt extrusion speed (rpm) | — | — | — | — | — | — |
| | | Melt extrusion time (min.) | — | — | — | 60 | 60 | 60 |
| | Apparent density (kg/L) | Before pretreatment | 0.05 | 0.03 | 0.09 | 0.05 | 0.03 | 0.09 |
| | | After pretreatment | — | — | — | 0.45 | 0.44 | 0.42 |
| Recycled raw material composition | HPLC (Area %) | MHET | 3.62 | 2.20 | 1.63 | 1.20 | 1.40 | 0.22 |
| | | BHET | 92.80 | 93.12 | 94.30 | 97.80 | 96.88 | 97.90 |
| | | DEG-ester-1 | 2.38 | 2.52 | 2.17 | 0.30 | 0.40 | 0.70 |
| | | DEG-ester-2 | 0.34 | 0.54 | 0.21 | 0.02 | 0.00 | 0.00 |
| | | HA-ester | 0.56 | 0.70 | 0.62 | 0.43 | 0.44 | 0.55 |

TABLE 2-continued

|  | C. Ex. 1 | C. Ex. 2 | C. Ex. 3 | C. Ex. 4 | C. Ex. 5 | C. Ex. 6 |
|---|---|---|---|---|---|---|
| Dimer | 0.27 | 0.84 | 0.79 | 0.16 | 0.68 | 0.24 |
| Trimer | 0.02 | 0.01 | 0.02 | 0.00 | 0.00 | 0.00 |
| Others | 0.0 | 0.1 | 0.3 | 0.1 | 0.2 | 0.4 |
| Pressurized filtration rate (L/min.) | 0.40 | 0.24 | 0.15 | 1.70 | 1.85 | 1.55 |
| Process yield (%) | 53.8 | 56.3 | 43.0 | 79.2 | 77.4 | 75.3 |

Referring to Tables 1 and 2 above, as the apparent density of a waste polyester, which was a raw material for depolymerization, was adjusted to 0.5 kg/L or more through a pretreatment procedure by melt extrusion, the depolymerization reaction was smoothly carried out, and the separation efficiency of insoluble components was improved even when the waste polyester contained heterogeneous components, as well as a single component, whereby a recycled raw material composition with high purity was prepared in high yield (see Examples 1 to 3).

However, when the pretreatment was performed without optimal control of the temperature, extrusion speed, and time at which melt extrusion was carried out, the waste polyester would be overly decomposed or not melted, making standardization impossible. Thus, it may be desirable to optimally control the conditions under which melt extrusion is carried out (see Examples 4 to 6).

Meanwhile, when a recycled raw material composition was prepared without carrying out a pretreatment procedure, a recycled raw material composition with a high content of impurities was prepared in a significantly low yield (see Comparative Examples 1 to 3). In addition, when the pretreatment procedure was carried out using a method other than melt extrusion, the apparent density of the waste polyester could not be adjusted to 0.5 kg/L or more; as a result, the purity and yield of the recycled raw material composition were lowered (see Comparative Examples 4 to 6).

The invention claimed is:

1. A process for preparing a recycled raw material composition, which comprises:
   (1) pretreating a waste polyester with an apparent density of 0.1 kg/L or less to have an apparent density of 0.5 kg/L or more;
   (2) depolymerizing the pretreated waste polyester; and
   (3) purifying a reactant obtained through the depolymerization,
   wherein step (2) comprises:
   (2-1) subjecting the waste polyester whose apparent density has been adjusted to depolymerization through a first glycolysis reaction at a temperature of 180 to 200° C. to obtain a first reactant; and
   (2-2) subjecting the first reactant to depolymerization at a temperature of 150 to 170° C. through a second glycolysis reaction to obtain a second reactant.

2. The process for preparing the recycled raw material composition of claim 1, wherein the pretreatment in step (1) is carried out through melt extrusion.

3. The process for preparing the recycled raw material composition of claim 2, wherein the melt extrusion is carried out at a temperature of 250 to 300° C. and an extrusion speed of 100 to 350 rpm for 2 to 15 minutes.

4. The process for preparing the recycled raw material composition of claim 2, wherein the melt extrusion is carried out without the addition of an additive.

5. The process for preparing the recycled raw material composition of claim 1, wherein the waste polyester whose apparent density has been adjusted to 0.5 kg/L or more in step (1) has a size of 5 mm or less and a cylindrical shape.

6. The process for preparing the recycled raw material composition of claim 1, wherein the waste polyester to be pretreated in step (1) comprises a waste polyester fabric, a waste polyester film, a waste polyester flake, a waste polyester powder, or a combination thereof.

7. The process for preparing the recycled raw material composition of claim 1, wherein step (3) comprises cooling the reactant to a temperature of 100 to 150° C. and pressurized-filtering the reactant at a pressure of 0.01 to 0.5 MPa, and the pressurized filtration rate of the cooled reactant is 1.5 L/minute or more.

8. The process for preparing the recycled raw material composition of claim 1, wherein step (3) comprises cooling and crystallizing the reactant.

9. The process for preparing the recycled raw material composition of claim 1, wherein step (3) comprises distilling the reactant.

10. The process for preparing the recycled raw material composition of claim 1, wherein, when the recycled raw material composition obtained through steps (1) to (3) is analyzed by high-performance liquid chromatography (HPLC), a total sum of a peak area fraction of diethylene glycol ester compounds and a peak area fraction of monohydroxyethyl terephthalate is less than 4.0%.

11. The process for preparing the recycled raw material composition of claim 1, wherein, when the recycled raw material composition obtained through steps (1) to (3) is analyzed by high-performance liquid chromatography (HPLC), a peak area fraction of an acetate-based ester compound is less than 0.4%.

12. The process for preparing the recycled raw material composition of claim 1, wherein, when the recycled raw material composition obtained through steps (1) to (3) is analyzed by high-performance liquid chromatography (HPLC), a peak area fraction of bis(2-hydroxyethyl) terephthalate is 95% or more.

13. The process for preparing the recycled raw material composition of claim 1, wherein a process yield (Y) according to the following Equation 1 is 80% or more:

$$Y\ (\%) = (W_1/W_2) \times 100 \qquad \text{[Equation 1]}$$

in Equation 1, $W_1$ is the weight of the recycled raw material composition obtained through steps (1) to (3), and $W_2$ is the theoretical weight of the recycled raw material composition prepared from the waste polyester used in step (1).

14. A recycled raw material composition, which is prepared by the preparation process of claim 1.

* * * * *